US00PP11978P2

(12) United States Plant Patent
Bergman

(10) Patent No.: US PP11,978 P2
(45) Date of Patent: Jul. 3, 2001

(54) HIBISCUS PLANT NAMED 'GOLDEN WIND'

(75) Inventor: Wendy R. Bergman, Lehigh Acres, FL (US)

(73) Assignee: Yoder Brothers, Inc., Barberton, OH (US)

( * ) Notice: Subject to any disclaimer, the term of this patent is extended or adjusted under 35 U.S.C. 154(b) by 0 days.

(21) Appl. No.: 09/333,126

(22) Filed: Jun. 14, 1999

(51) Int. Cl.[7] ..... A01H 5/00
(52) U.S. Cl. ..... Plt./257
(58) Field of Search ..... Plt./257

*Primary Examiner*—Bruce R. Campell
*Assistant Examiner*—Michelle Kizilkaya
(74) *Attorney, Agent, or Firm*—C. A. Whealy

(57) ABSTRACT

A new and distinct cultivar of Hibiscus plant named 'Golden Wind', characterized by its very glossy, undulate, very dark green leaves; upright, compact, outwardly spreading, uniform, dense and symmetrical plant habit that is appropriate for container production; very freely flowering; numerous golden yellow-colored flowers with red "eyes"; short peduncles; good resistance to flower bud abscission; relative resistance to diseases common to Hibiscus grown under Florida production conditions; and excellent postproduction longevity.

2 Drawing Sheets

BACKGROUND OF THE INVENTION

The present invention relates to a new and distinct cultivar of Hibiscus, botanically known as *Hibiscus rose-sinensis* and hereinafter referred to by the cultivar name Golden Wind.

The new Hibiscus is a product of a planned breeding program conducted by the Inventor in Alva, Fla. The objective of the breeding program is to create new freely-branching Hibiscus cultivars with uniform and compact plant habit appropriate for container production, ealry and uniform flowering, numerous flowers per lateral branch, desirable flower color, resistance to flower bud abscission, and good postproduction longevity.

The new Hibiscus originated from a cross made by the Inventor in Alva, Fla., of a proprietary *Hibiscus rosa-sinensis selection*, designated as code number YB-1242, as the female, or seed, parent with the *Hibiscus rosa- sinensis* cultivar Light Wind, disclosed in U.S. Plant Pat. No. 10,593, as the male, or pollen, parent. The cultivar Golden Wind was discovered and selected by the Inventor as a flowering plant within the progeny of the stated cross in a controlled environment in Alva, Fla., on Sep. 29, 1995.

Compared to plants of the white-flowered female parent, the proprietary Hibiscus selection code number YB-1242, plants of the new Hibiscus are more upright; have smaller and darker green foliage; and are less attractive to whiteflies. Plants of new Hibiscus flower about 4 to 6 days later; are less susceptible to diseases common to Hibiscus grown under Florida production conditions; and differ in flower color compared to plants of the male parent, the cultivar Light Wind.

Plants of the new Hibiscus are distinguished from its sibling, the cultivar Coconut Wind, U.S. Plant Patent application Ser. No. 09/333,128 with this application, in flower color.

Asexual reproduction of the new Hibiscus by terminal cuttings taken in a controlled environment in Alva, Fla., has shown that the unique features of this new Hibiscus are stable and reproduced true type in successive generations.

SUMMARY OF THE INVENTION

The cultivar Golden Wind has not been observed under all possible environmental conditions. The phenotype may vary somewhat with variations in environment such as temperature, light intensity, nutrition and water status without, however, any variance in genotype.

The following traits have been repeatedly observed and are determined to be the unique characteristics of 'Golden Wind'. These characteristics in combination distinguish 'Golden Wind' as a new and distinct cultivar:

1. Very glossy, undulate, very dark green leaves.
2. Upright, compact, outwardly spreading, uniform, dense and symmetrical plant habit that is appropriate for container production.
3. Very freely flowering, numerous golden yellow-colored flowers with red "eyes" and short peduncles.
4. Good resistance to flower bud abscission.
5. Relatively resistant to pathogens common to Hibiscus grown under Florida production conditions.
6. Excellent postproduction longevity.

Plants of the new Hibiscus can be compared to plants of the cultivar Sundance, not patented. However, in side-by-side comparsions conducted in Alva, Fla., plants of the new Hibiscus differ from plants of the cultivar Sundance in the following characteristics:

1. Plants of the new Hibiscus are more upright than plants of the cultivar Sundance.
2. Plants of the new Hibiscus have smaller leaves than plants of the cultivar Sundance.
3. Flowers of plants of the new Hibiscus are smaller than flowers of plants of the cultivar Sundance.
4. Plants of the new Hibiscus and the cultivar Sundance differ in "eye" or throat color.

Plants of the new Hibiscus also can be compared to plants of the cultivar Sahara Wind, disclosed in U.S. Plant Pat. No. 10,879. However, in side-by-side comparisons conducted in Alva, Fla., plants of the new Hibiscus differ from plants of the cultivar Sahara Wind in the following characteristics:

1. Plants of the new Hibiscus are more upright than plants of the cultivar Sahara Wind.

2. Plants of the new Hibiscus have darker green and much smaller leaves than plants of the cultivar Sahara Wind.
3. Flowers of plants of the new Hibiscus are smaller than flowers of plants of the cultivar Sahara Wind.
4. Plants of the new Hibiscus are less attractive to whiteflies than plants of the cultivar Sahara Wind.

BRIEF DESCRIPTION OF THE PHOTOGRAPHS

The accompanying colored photographs illustrate the overall appearance of the new Hibiscus, showing the colors as true as it is reasonably possible to obtain in colored reproductions of this type.

The photograph on the first sheet comprises a side perspective view of a typical plant of 'Golden Wind'.

The photograph on the second sheet comprises a close-up view of a typical flower of 'Golden Wind'. Both photographs were taken when plants were about 7 months old. Flower and foliage colors in the photographs may appear different from the actual colors due to light reflectance.

DETAILED BOTANICAL DESCRIPTION

The following observations, measurements and values describe plants grown in Alva, Fla, with five plants per 16.5-cm containers, in polyethylene-covered greenhouses during the late spring under conditions which closely approximate commerical production. Night temperatures ranged between 13 to 24° C. and day temperatures ranged between 21 and 32° C. Plants were about 7 months old when the descriptions were taken. In the description, color references are made to The Royal Horicultural Society Colour Chart except where general terms of ordinary dictionary significance are used.

Botanical classification *Hibiscus rosa-sinensis* cultivar Golden Wind.

Parentage:

*Female or seed parent.*—*Hibiscus rosa-sinensis* proprietary selection designated as code number YB-1242.

*Male or pollen parent.*—*Hibiscus rosa-sinensis* cultivar Light Wind, disclosed in U.S. Plant Pat. No. 10,593.

Propagation:

*Type.*—By terminal cuttings.

*Time to initiate roots.*—About 10 days at temperatures of 24° C.

*Time to develop roots.*—About 28 days at temperatures of 24° C.

*Rooting habit.*—Moderately vigorous, thick and well-branched.

Plant description:

*Plant form and growth habit.*—Perennial, evergreen, upright, outwardly spreading, compact, uniform, dense and symmetical plant habit.

*Branching habit.*—Freely branching, usually about four lateral branches develop after removal of terminal apex.

*Plant height, soil level to top of flowers.*—About 25 cm.

*Plant diameter, area of spread.*—About 45 cm.

*Lateral branch description.*— Length: About 21 cm. Diameter: About 5.5 mm. Texture: Immature, smooth; mature, woody and rough. Color: Immature: Green, 146A. Mature: Brown, 200A to 200B.

Foliage description:

*Arrangement.*—Alternate, single; numerous; symmetrical.

*Length.*—About 8.5 cm.

*Width.*—About 5.4 cm.

*Shape.*—Ovate.

*Apex.*—Narrowly acute.

*Base.*—Obtuse to slightly cordate.

*Margin.*—Serrate.

*Aspect.*—Undulate.

*Texture.*—Glabrous and glossy on both surfaces.

*Color.*—Young foliage, upper surface: Darker and greener than 146A. Young foliage, lower surface: Close to 146A. Mature foliage, upper surface: Much darker than 147A. Mature foliage, lower surface: 147A.

*Petiole.*—Length: About 3.1 cm. Diameter: About 3 mm. Texture: Mostly smooth with very fine pubescence on upper surface. Color: 200A to 200B.

Flower description:

*Natural flowering season.*—Usually spring and summer or during periods of warm weather.

*Flower arrangement.*—Flowers arranged singly at terminal leaf axils. Very freely flowering with usually about three or four flower buds and /or open flowers per terminal apex. Flowers face upright and slightly outward.

*Flower appearance.*—Rounded, golden yellow-colored petals with red "eye". Flowers are open for about one day before closing. Flowers persistent.

*Flower diameter.*—About 11.5 cm.

*Flower bud (just before showing color).*— Rate of opening: About one or two days depending on temperatures. Length: About 3.2 cm. Diameter: About 1.2 cm. Shape: Elliptic.

*Petals.*—Texture: Smooth, satiny. Arrangement: Corolla consists of five petals that overlap. Shape: Spatulate with rounded apex. Margin: Entire, but slightly ruffled. Length: About 8.2 cm. Width: About 6 cm. Color: Upper surface: Golden yellow, 14A to 14B. Lower surface: Golden yellow, 14A to 14B. Throat or "eye": Red, 45A; glossy.

*Sepals.*— Appearance: Five sepals fused into a star-shaped calyx. Shape: Linear. Texture: Slightly pubescent. Color, outer surface: 146A.

*Bracts.*— Appearance: About eight fused at base. Length: About 1.2 cm. Width: About 3 mm. Shape; Linear. Color: 147A.

*Peduncles.*— Length: Short, about 3 cm. Diameter: About 3 mm at base. Angle: Upright to slightly bent. Strength: Strong, flexible. Texture: Slightly pubescent. Color: Above knuckle, green, 146A; below knuckle green, 146A, with brown overtones.

*Reproductive organs.*— Androecium: Stamen number: Numerous, about 57. Stamen length: About 5 mm. Filament color: 12A. Anther size: About 1 mm by 0.5 mm. Amount of pollen: Abundant. Pollen color: 14A. Gynoecium: Pistil length: About 9.25cm. Style color: Base, 17A; midsection and apex, 12A. Stigma appearance: Five, rounded. Stigma diameter: About 2 mm. Stigma color: Close to 23A.

Disease resistance: Plants of the new Hibiscus grown under Florida production conditions have shown to be relatively resistant to pathogens common to Hibiscus.

Seed Production: Seed production has not been observed.

It is claimed:

1. A new and distinct Hibiscus plant named 'Golden Wind', as illustrated and described.

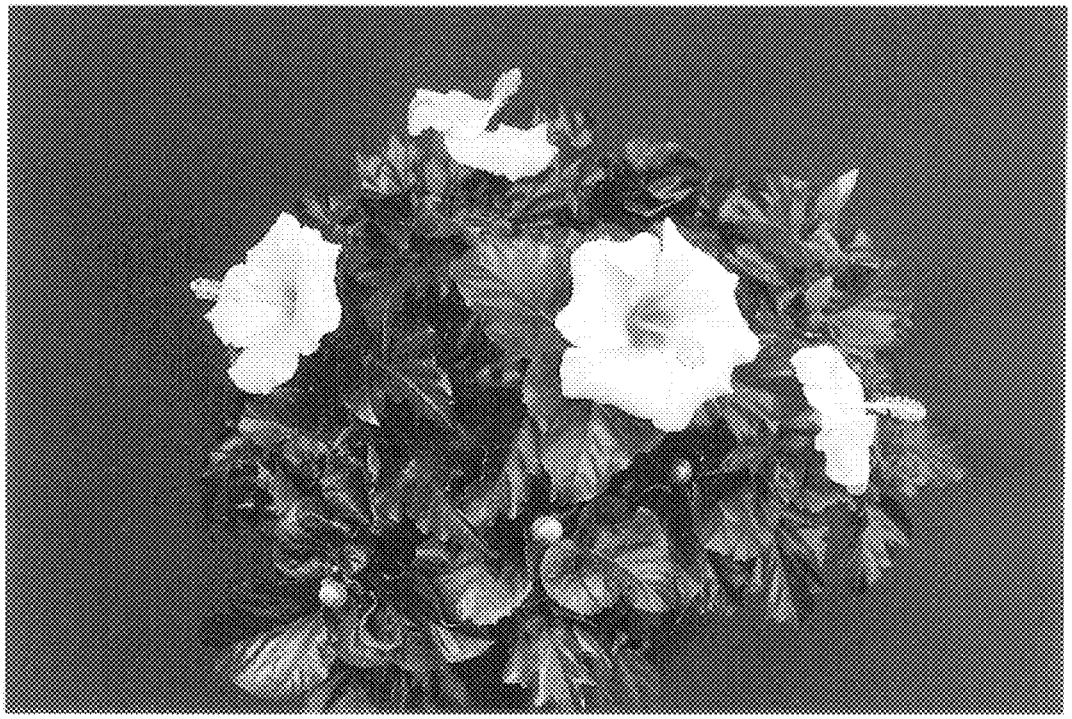

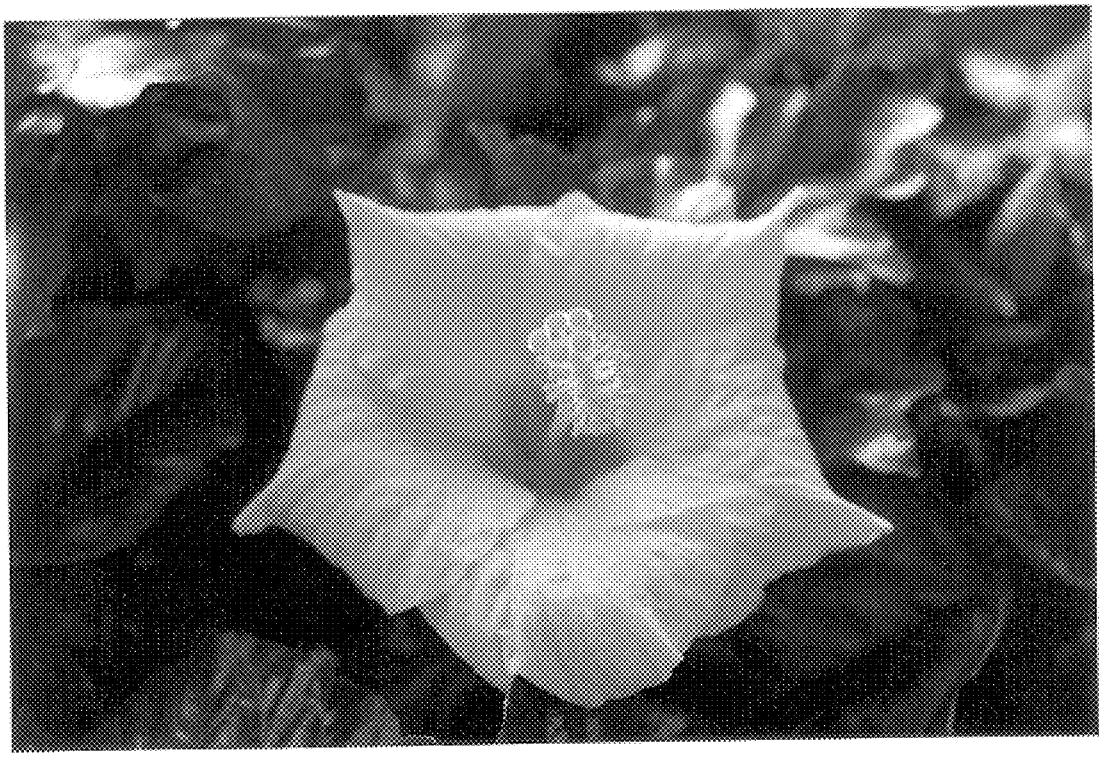

* * * * *